(12) United States Patent
Appareti et al.

(10) Patent No.: US 11,471,638 B2
(45) Date of Patent: Oct. 18, 2022

(54) PRESSURE SUPPORT SYSTEM VALVE

(71) Applicant: KONINKLIJKE PHILIPS N.V., Eindhoven (NL)

(72) Inventors: Karl Appareti, Pittsburgh, PA (US); Christopher Allen Gorman, Pittsburgh, PA (US); Bin Zhang, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 405 days.

(21) Appl. No.: 16/684,629

(22) Filed: Nov. 15, 2019

(65) Prior Publication Data
US 2020/0155876 A1    May 21, 2020

Related U.S. Application Data

(60) Provisional application No. 62/768,164, filed on Nov. 16, 2018.

(51) Int. Cl.
*A61M 16/10*    (2006.01)
*A61M 16/12*    (2006.01)
*A61M 16/20*    (2006.01)
*A61M 16/08*    (2006.01)
*A61M 16/00*    (2006.01)
*A61M 16/06*    (2006.01)
(Continued)

(52) U.S. Cl.
CPC .... *A61M 16/0816* (2013.01); *A61M 16/1095* (2014.02); *A61M 16/122* (2014.02); *A61M 16/16* (2013.01); *A61M 16/208* (2013.01); *A61M 16/0069* (2014.02); *A61M 16/06* (2013.01); *A61M 16/0875* (2013.01); *A61M 16/101* (2014.02); *A61M 16/205* (2014.02); *A61M 2016/0027* (2013.01); *A61M 2202/0208* (2013.01); *A62B 9/02* (2013.01)

(58) Field of Classification Search
CPC .............. A61M 16/00; A61M 16/0057; A61M 16/0066; A61M 16/0816; A61M 16/101; A61M 16/1095; A61M 16/12; A61M 16/123; A61M 16/16; A61M 16/20; A61M 16/208; A61M 39/26; A61M 2039/2406; A61M 2039/261
See application file for complete search history.

(56) References Cited

U.S. PATENT DOCUMENTS 5,878,743 A * 3/1999 Zdrojkowski ............ A62B 9/02
128/204.23
5,896,857 A    4/1999 Hely et al.
(Continued)

*Primary Examiner* — Joseph D. Boecker
(74) *Attorney, Agent, or Firm* — Michael W. Haas

(57) ABSTRACT

The present disclosure describes a pressure support therapy device valve that enables a subject to safely supplement therapy pressure support with low flow oxygen while using a heated (or non-heated) tube. The valve conducts a pressurized flow of breathable gas and the low flow oxygen to the heated tube. The valve includes electrical components configured to pass power from the pressure support therapy device to the heated tube, and a plunger biased to close a flow path from the pressure support therapy device when a pressurized flow of breathable gas is not provided (or is below a predetermined pressure threshold). Closing the flow path stops oxygen gas from flowing back through the valve toward the pressurized gas source.

15 Claims, 5 Drawing Sheets

(51) Int. Cl.
*A61M 16/16* (2006.01)
*A62B 9/02* (2006.01)

(56) References Cited

U.S. PATENT DOCUMENTS

| | | | |
|---|---|---|---|
| 8,710,682 B2 | 4/2014 | Dershem et al. | |
| 9,923,442 B2 | 3/2018 | Chalvignac | |
| 9,974,917 B2 | 5/2018 | Bafile et al. | |
| 10,086,166 B1* | 10/2018 | Nashed | A61M 16/104 |
| 2001/0017134 A1 | 8/2001 | Bahr | |
| 2006/0124127 A1* | 6/2006 | Du | A61M 16/085 |
| | | | 128/201.13 |
| 2009/0260629 A1 | 10/2009 | Yee et al. | |
| 2012/0085348 A1* | 4/2012 | Chalvignac | A61M 16/1095 |
| | | | 128/204.21 |
| 2012/0125333 A1 | 5/2012 | Bedford et al. | |
| 2012/0152254 A1 | 6/2012 | Smith et al. | |
| 2015/0306332 A1* | 10/2015 | Bafile | A61M 16/0875 |
| | | | 128/202.27 |
| 2015/0320962 A1* | 11/2015 | Bafile | A61M 16/0638 |
| | | | 128/204.18 |
| 2016/0074607 A1* | 3/2016 | Ratner | A61M 16/207 |
| | | | 128/204.23 |
| 2018/0361100 A1 | 12/2018 | Holley et al. | |

* cited by examiner

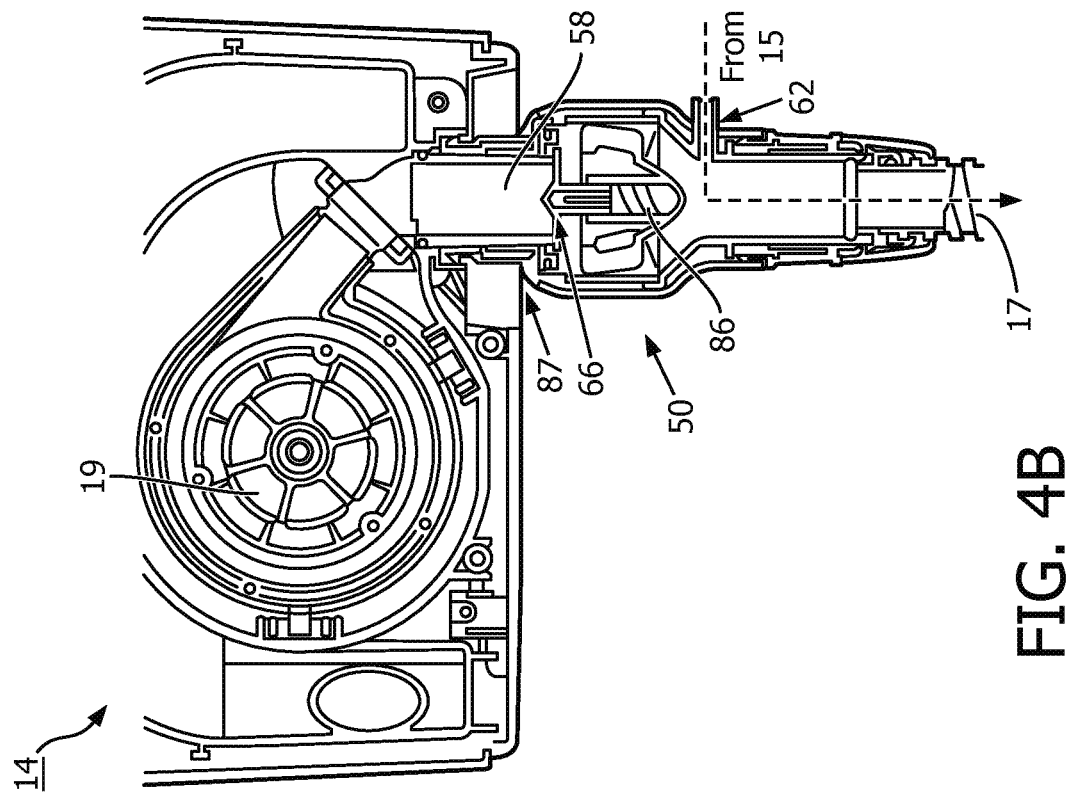
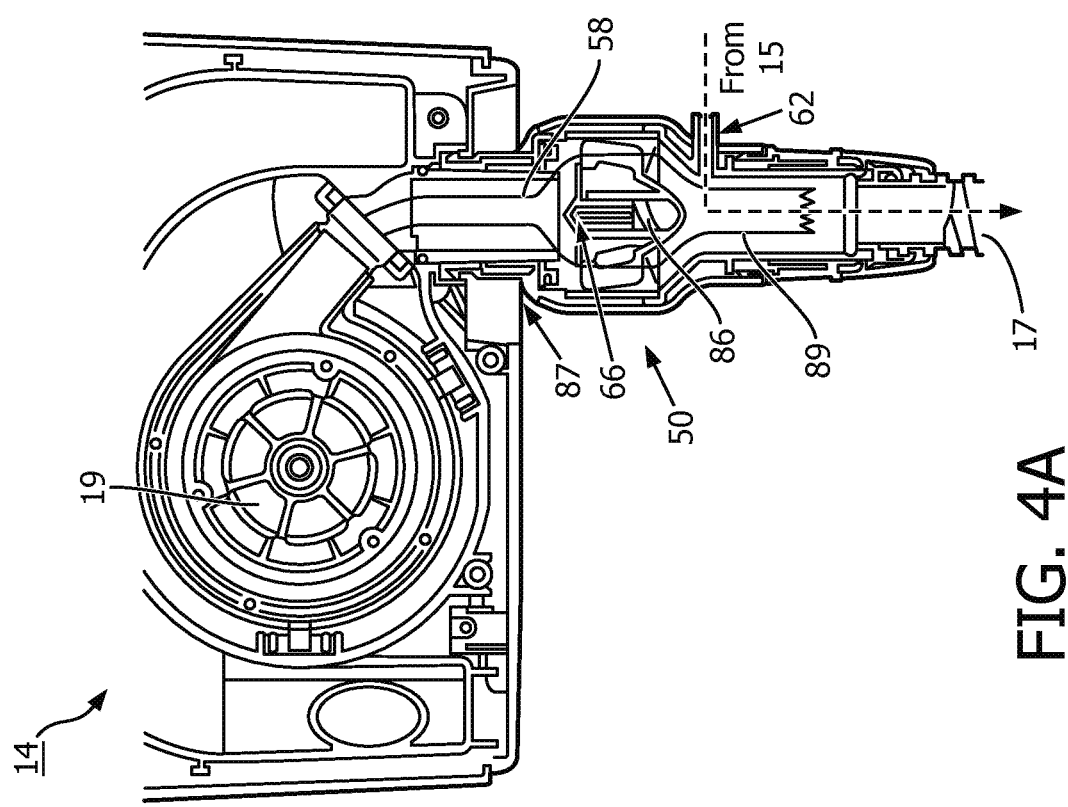

PRESSURE SUPPORT SYSTEM VALVE

CROSS-REFERENCE TO RELATED APPLICATIONS

This patent application claims the priority benefit under 35 U.S.C. § 119(e) of U.S. Provisional Application No. 62/768,164 filed on Nov. 16, 2018, the contents of which are herein incorporated by reference.

BACKGROUND

1. Field

The present disclosure pertains to a pressure support therapy device valve that enables a subject to supplement therapy pressure support with low flow oxygen with or without a heated tube.

2. Description of the Related Art

Pressure support therapy is known. Supplemental oxygen is often provided with pressure support therapy. One-way mechanically actuated valves are used to prevent oxygen flow back into a pressure generating device during pressure support therapy. One such valve is described in U.S. Pat. No. 8,710,682. Heated tubes may be used to deliver the pressure support therapy and the supplemental oxygen to a subject. However, using a heated tube with supplemental oxygen during pressure support therapy currently requires equipment adjustments to ensure subject safety during pressure support therapy.

SUMMARY

It would be advantageous for a subject to be able use a heated tube with supplemental oxygen during pressure support therapy without a need for equipment adjustments to ensure subject safety.

Accordingly, one or more aspects of the present disclosure relate to a valve configured for use in a pressure support therapy system. The pressure support therapy system comprises a pressurized gas source, a supplemental gas source, a subject interface with a heated tube, and/or other components. The valve comprises an inlet cap, a body, an outlet cap, and/or other components. The inlet cap comprises a first electrical connector and a first flow path, both configured to removably couple with the pressurized gas source. The first flow path is configured to receive a pressurized flow of breathable gas from the pressurized gas source. The first electrical connector is configured to receive electrical power from the pressurized gas source.

The body is coupled to the inlet cap. The body comprises a channel configured to receive the pressurized flow of breathable gas from the first flow path, and a plunger biased to close the first flow path in the inlet cap when the pressurized flow of breathable gas is not provided by the pressurized gas source or is provided at a pressure that is below a predetermined pressure threshold. Closing the first flow path stops supplemental therapy gas from flowing through the inlet cap toward the pressurized gas source when the inlet cap is coupled to the pressurized gas source.

The outlet cap is coupled to the body. The outlet cap comprises a side orifice configured to receive the supplemental therapy gas from the supplemental gas source. The outlet cap includes a second electrical connector electrically coupled with the first electrical connector, and a second flow path coupled with the channel. The outlet cap is configured to removably couple with the heated tube such that the second flow path conducts the pressurized flow of breathable gas and the supplemental therapy gas from the channel to the heated tube, and the second electrical connector conducts the electrical power from the gas source to the heated tube when the outlet cap is coupled to the heated tube.

In some embodiments, the valve further comprises a cover configured to cover the body, at least a portion of the inlet cap, and at least a portion of the outlet cap. In some embodiments, the cover comprises two pieces forming opposite sides of the valve.

In some embodiments, the valve further comprises one or more vents in the body. The vents are configured to vent the channel to atmosphere to facilitate dispersion of the supplemental therapy gas to atmosphere and breathing of atmospheric air by a subject when the plunger has closed the first flow path in the inlet cap. In some embodiments, the body comprises an outer cylinder and an inner cylinder. The outer cylinder forms the channel. The inner cylinder is coupled to the plunger and the one or more vents, and in communication with the channel, such that the channel is vented to atmosphere when the plunger closes the first flow path in the inlet cap, and substantially sealed from atmosphere when the pressurized flow of breathable gas is provided by the pressurized gas source.

In some embodiments, the body further comprises a spring coupled to the plunger. The spring is configured to bias the plunger to close the first flow path in the inlet cap. In some embodiments, a spring force of the spring is configured such that the plunger closes the first flow path in the inlet cap when a pressure of the pressurized flow of breathable provided by the pressurized gas source is less than the predetermined pressure threshold.

In some embodiments, the valve further comprises a silicone radial seal positioned in the inlet cap before the body. The silicone radial seal is configured to substantially seal a connection between the inlet cap and the pressurized gas source such that the pressurized flow of breathable gas and/or the supplemental therapy gas do not unintentionally leak out of the valve.

Another aspect of the present disclosure relates to a method for controlling flow in the pressure support therapy system with the valve. The method comprises removably coupling the first electrical connector and the first flow path of the inlet cap with the pressurized gas source. The method comprises receiving supplemental therapy gas from the supplemental gas source with the side orifice of the outlet cap. The method comprises receiving the pressurized flow of breathable gas from the first flow path and the supplemental therapy gas from the side orifice. The method comprises closing, with the plunger of the body, the first flow path in the inlet cap when the pressurized flow of breathable gas is not provided by the pressurized gas source or is provided at a pressure that is below the predetermined pressure threshold. The method comprises coupling the second electrical connector of the outlet cap with the first electrical connector of the inlet cap, and the second flow path in the outlet cap with the channel in the body. The outlet cap is configured to removably couple with the heated tube such that the second flow path conducts the pressurized flow of breathable gas and the supplemental therapy gas from the channel to the heated tube and the second electrical connector conducts the electrical power from the gas source to the heated tube when the outlet cap is coupled to the heated tube.

In some embodiments, the method further comprises venting, with the one or more vents of the body, the channel to atmosphere to facilitate dispersion of the supplemental therapy gas to atmosphere and breathing of atmospheric air by the subject when the plunger has closed the first flow path in the inlet cap.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 4A illustrates an open configuration of the valve, in accordance with one or more embodiments;

FIG. 4B illustrates a closed configuration of the valve, in accordance with one or more embodiments.

DETAILED DESCRIPTION OF EXEMPLARY EMBODIMENTS

Figure 1:
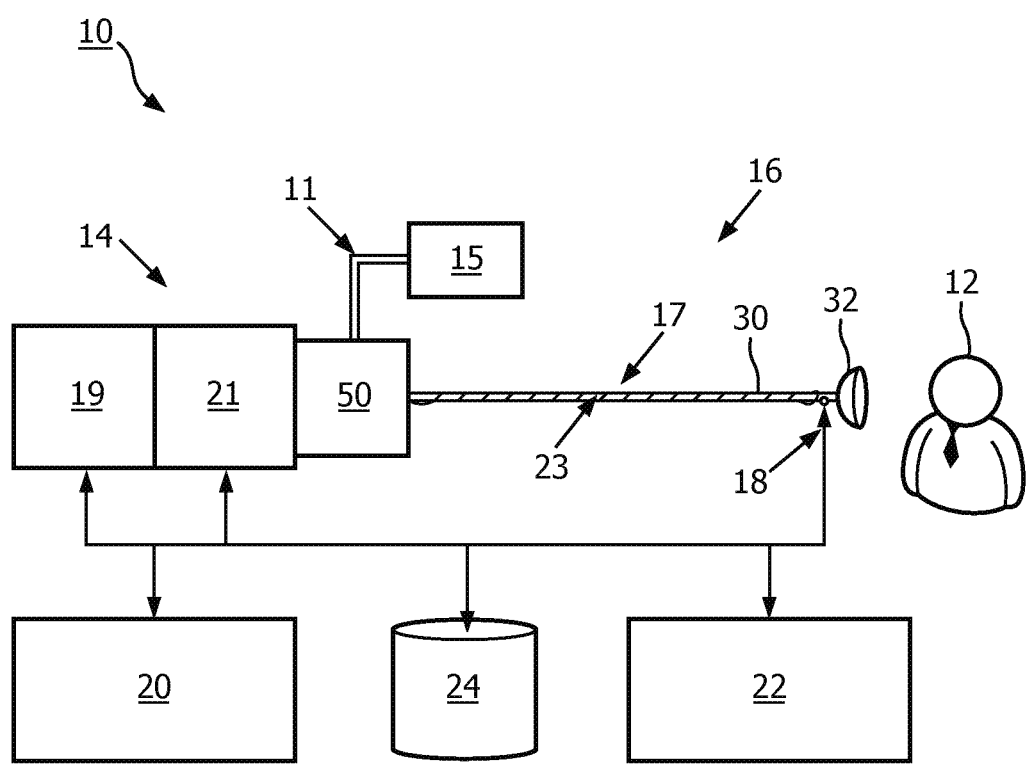
FIG. 1 illustrates a pressure support system, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a pressure support system 10. In some embodiments, system 10 comprises one or more of pressurized gas source 14, a source 15 of supplemental therapy gas, a subject interface 16 including a heated tube 17, a sensor 18, a controller 20, a user interface 22, electronic storage 24, a valve 50, and/or other components. Supplemental therapy gas (e.g., oxygen) is often prescribed in conjunction with pressure support therapy for many subjects. Regulations require oxygen concentrations in pressure support therapy devices to be below an oxygen concentration threshold (e.g., 25% oxygen) in areas of the device close to electrical components, or any other ignition sources. This means that oxygen back-flow into a pressurized gas source during delivery of supplemental oxygen (or other supplemental therapy gasses) should be prevented.

Pressure support therapy devices are often designed with comfort features to make therapy more enjoyable for a subject. One such feature is a heated tube used in conjunction with a humidifier to deliver warm, humid air to the subject. Currently available oxygen (for example) enrichment adaptors and valves do not facilitate the use of heated tubes with supplemental oxygen or other therapy gasses at least because there are no electrical bridges to pass power from the device to the heated tube in these adaptors and valves. One solution to solve this problem has been to integrate the oxygen port into the heated tube itself. Another solution has been to supply oxygen directly to the mask of the subject, bypassing the heated tube entirely. However, subjects need a specialty device or tube (to integrate an oxygen port into a heated tube), and/or mask (configured to receive the supplemental therapy gas from a source other than the heated tube) to effectively utilize these solutions.

In contrast to prior systems, valve 50 integrates a one-way valve, a supplemental therapy gas (e.g., oxygen) enrichment adaptor, and electrical connections into a single device that allows a subject 12 to safely use heated tube 17 with supplemental oxygen and/or other therapy gasses. Valve 50 prevents oxygen (for example) from flowing back into pressurized gas source 14 when pressure support therapy pressures are not delivered. Valve 50 safely prevents oxygen backflow into the pressurized gas source 14, while keeping subject 12 comfortable because there are no additional tubes or adaptors that are required to be connected to subject interface 16 to use supplemental therapy gas or a heated tube. For example, subject 12 may simply couple an inlet of valve 50 to an outlet of pressurized gas source 14, couple an existing heated tube 17 to an outlet of valve 50, couple a supplemental therapy gas (oxygen) tube to valve 50, fit a mask to heated tube 17, and begin therapy as usual.

Pressurized gas source 14 is configured to generate a pressurized flow of breathable gas for delivery to the airway of subject 12. Pressurized gas source 14 may control one or more parameters of the flow of gas (e.g., flow rate, pressure, volume, temperature, humidity, duration, a timing, gas composition, etc.) for therapeutic purposes, and/or for other purposes. Pressurized gas source 14 may include a pressure generator 19, a humidifier 21, and/or other components. Pressure generator 19 receives a flow of gas from a gas source, such as the ambient atmosphere, and elevates and/or reduces the pressure of that gas for delivery to the airway of subject 12. Pressurized gas source 14 includes any device, such as, for example, a pump, a blower, a piston, or bellows, that is capable of elevating and/or reducing the pressure of the received gas for delivery to subject 12. Pressurized gas source 14 may comprise one or more valves for controlling the pressure and/or flow of gas, for example. The present disclosure also contemplates controlling the operating speed of pressure generator 19, either alone or in combination with such valves, to control the pressure and/or flow of gas provided to subject 12.

Humidifier 21 is configured to humidify the pressurized flow of breathable gas. Humidifier 21 may comprise a humidification chamber, a gas inlet, a gas outlet, a heating element, and/or other components. In some embodiments, humidifier 21 is a warm mist humidifier (e.g., a vaporizer) configured to generate water vapor by heating liquid held within humidifier 21 via a heating element. Humidifier 21 may comprise an inductive heater configured to heat the liquid held within humidifier 21 via inductive heating. In some embodiments, humidifier 21 may be a pass-over humidifier, a vibratory humidifier, and/or any other type of humidifier that allows the present system to function as described herein. Humidifier 21 is configured such that the flow of gas is received from pressure generator 19 by humidifier 21 through a gas inlet and is humidified within a humidification chamber by the water vapor before being released from the humidification chamber through a gas outlet. The gas outlet of the humidifier is coupled with valve 50 such that the humidified flow of gas is delivered to the airway of subject 12 through subject interface 16.

Figure 2A:
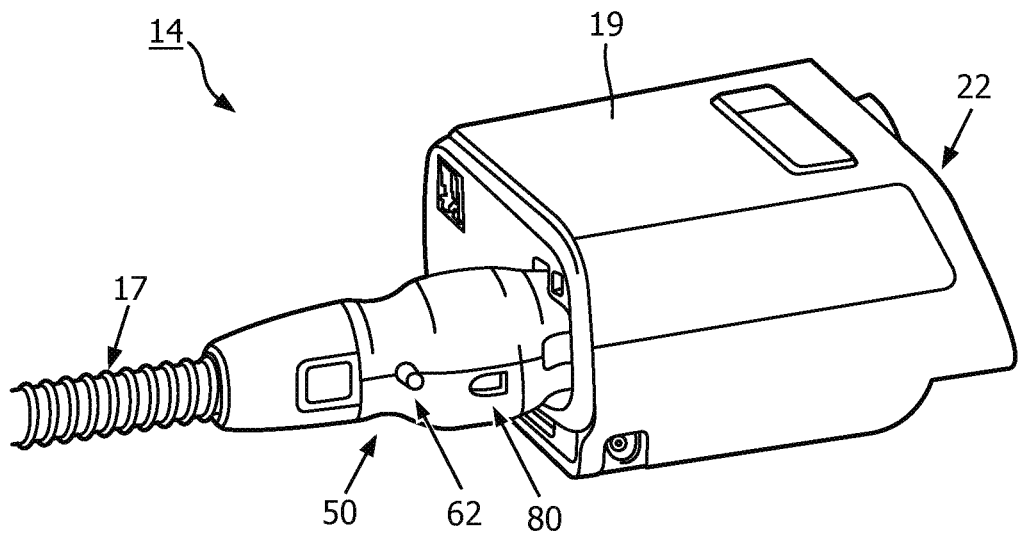
FIG. 2A illustrates a valve of the system coupled to a pressure generator, in accordance with one or more embodiments.
Figure 2B:
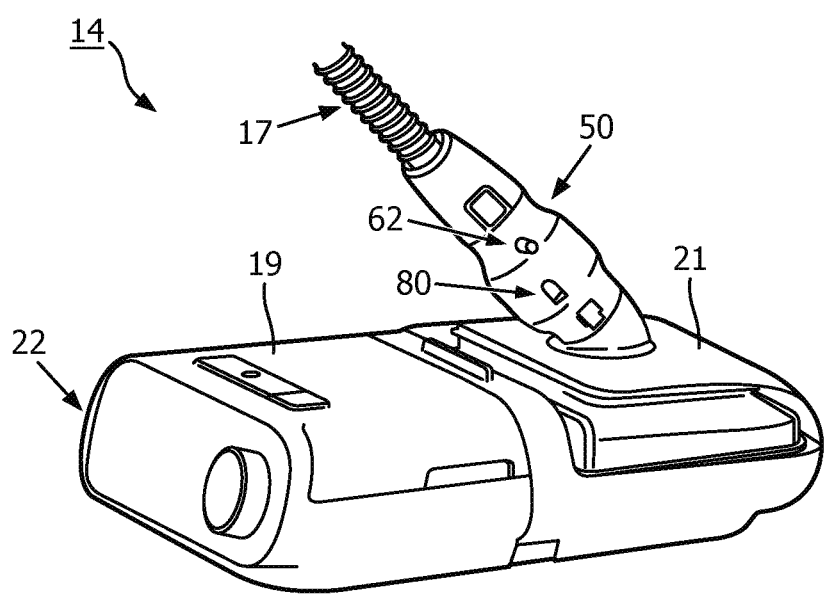
FIG. 2B illustrates the valve coupled to a humidifier, in accordance with one or more embodiments.

FIGS. 2A and 2B illustrate valve 50 coupled to pressurized gas source 14. As shown in FIGS. 2A and 2B, valve 50 is configured to couple with pressure generator 19 or humidifier 21 such that valve 50 may be used with embodiments of system 10 that include or do not include humidifier 21. FIG. 2A illustrates valve 50 coupled to pressure generator 19. FIG. 2B illustrates valve 50 coupled to humidifier 21. In both embodiments, valve 50 is also coupled to heated tube 17. FIGS. 2A and 2B also illustrate side orifice 62 configured to receive supplemental therapy gas (e.g., oxygen), a vent 80 configured to vent an interior of valve 50 to atmosphere, and an embodiment of (or a portion of an embodiment of) user interface 22 (all described below).

Returning to FIG. 1, supplemental gas source 15 may comprise a source of oxygen and/or another supplemental therapy gas. Supplemental gas source 15 may be coupled to valve 50 by a conduit 11 and/or other components. In some embodiments, this coupling may comprise a removable attachment. In some embodiments, coupling may be accomplished through added plumbing and/or additional manufactured parts to couple supplemental gas source 15 to valve 50. In some embodiments, the supplemental therapy gas may be contained in, for example, a tank, a canister, and/or other portable containers separate from system 10. In these embodiments, the additional container may be portable, rechargeable, and/or replaceable. In some embodiments, the portable, rechargeable, and/or replaceable supply of supplemental therapy gas may be included within system 10. In some embodiments, supplemental gas source 15 may be and/or include an oxygen concentrator and/or other gas generation systems. The oxygen concentrator and/or other gas generation systems may be a separate component external to system 10 or the oxygen concentrator and/or other has generation systems may be an integrated part of system 10.

Sensors 18 are configured to generate output signals conveying information related to one or more gas parameters of the pressurized flow of breathable gas, one or more breathing parameters related to the respiration of subject 12, and/or other information. The one or more gas parameters and/or the one or more breathing parameters may comprise one or more of a flow rate, a volume, a pressure, a composition (e.g., concentration(s) of one or more constituents), temperature, humidity, acceleration, velocity, acoustic parameters, parameters indicative of respiratory effort by subject 12, a timing, a duration, a frequency, and/or other parameters. Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressurized gas source 14 (e.g., a valve driver or motor current, voltage, rotational velocity, and/or other operating parameters). Although sensors 18 are illustrated at a single location within (or in communication with) conduit 30 between interface appliance 32 and pressurized gas source 14, this is not intended to be limiting. Sensors 18 may include sensors disposed in a plurality of locations, such as for example, within pressurized gas source 14, within (or in communication with) interface appliance 32, in communication with subject 12, and/or in other locations.

Subject interface 16 is configured to deliver the pressurized flow of breathable gas to the airway of subject 12. As such, subject interface 16 comprises heated tube 17, an interface appliance 32, and/or other components. Heated tube 17 includes conduit 30, a heat source 23, and/or other components. Conduit 30 is configured to convey the pressurized flow of gas to interface appliance 32. Conduit 30 may be a flexible length of hose, or other conduit, that places interface appliance 32 in fluid communication with pressurized gas source 14.

Heat source 23 is configured to controllably heat the pressurized flow of breathable gas in subject interface 16. Heat source 23 is illustrated in FIG. 1 within (or in communication with) conduit 30 running between valve 50 and interface appliance 32. The illustrated position of heat source 23 is not intended to be limiting. Heat source 23 may be located in any position that allows it to controllably heat the pressurized flow of breathable gas in subject interface 16. Heat source may be configured to heat the pressurized flow of breathable gas continuously along the entire length of conduit 30, for example. Heat source 23 may be configured to heat the pressurized flow of breathable gas by dissipating electrical current (e.g., resistive heating), and/or by other methods. Heat source 23 may comprise one or more of a heating coil, a heating jacket, heating tape, and/or other heating devices. Heat source 23 may be configured to heat the gas in subject interface 16 directly and/or indirectly. In some embodiments, a heating coil may be positioned within conduit 30 in fluid communication with the pressurized flow of breathable gas to directly heat the gas flow. In some embodiments, a heating jacket may be placed around conduit 30 to heat the flow of gas indirectly by transferring heat through the wall of conduit 30.

Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

Figure 3:
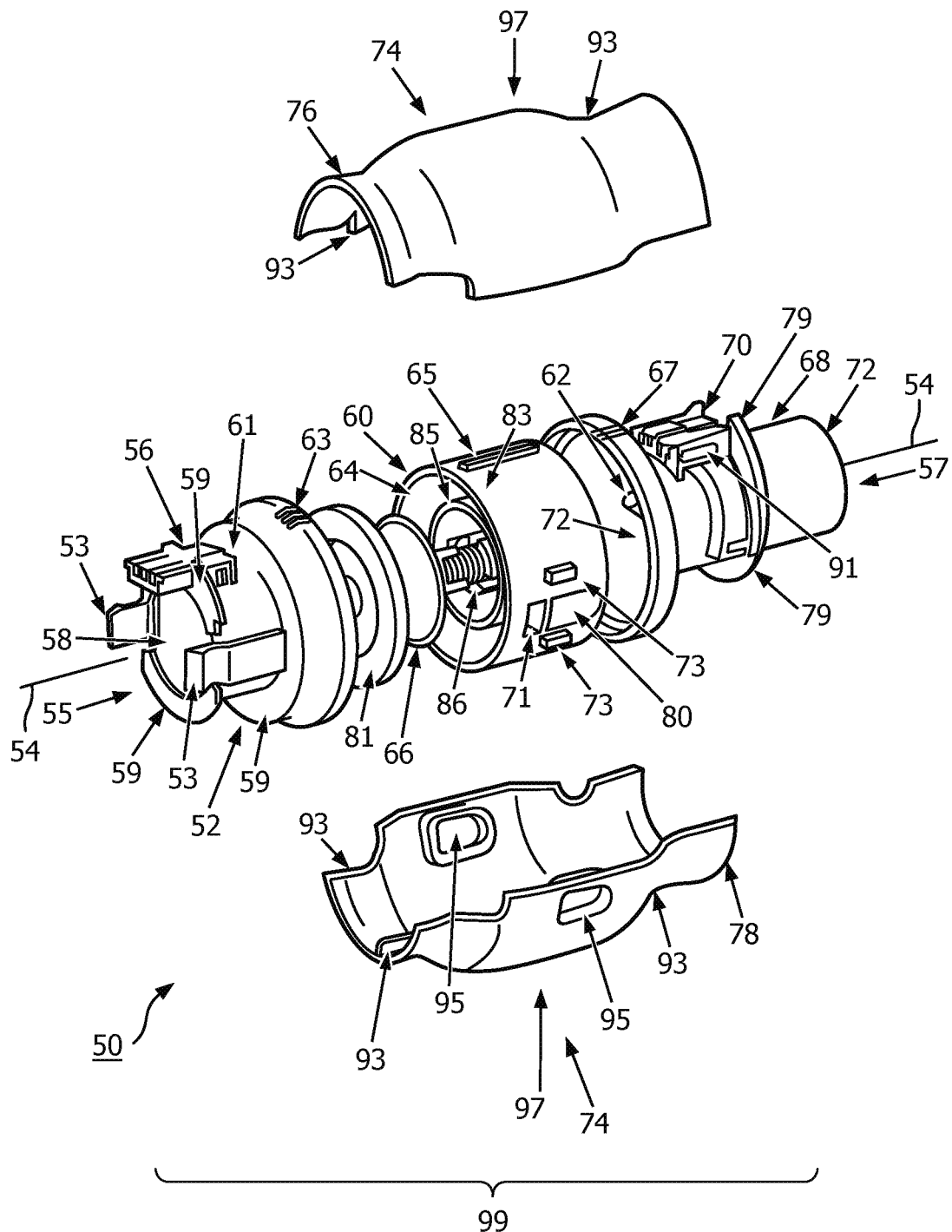
FIG. 3 illustrates an exploded view of the valve, in accordance with one or more embodiments.

Valve 50 is configured to control the pressurized flow of breathable gas from pressurized gas source 14, and the supplemental therapy gas from supplemental gas source 15, to heated tube 17. FIG. 3 illustrates an exploded view of valve 50. As shown in FIG. 3, valve 50 comprises an inlet cap 52, a body 60, an outlet cap 68 and/or other components. In some embodiments, inlet cap 52, body 60, and outlet cap 68 each have a generally cylindrical cross-sectional shape. In some embodiments, inlet cap 52 is formed along an axis 54 of valve 50, body 60 is coupled to inlet cap 52 positioned along axis 54 of valve 50, and outlet cap 68 is coupled to body 60 opposite inlet cap 52 along axis 54 of valve 50.

Inlet cap 52 is configured to be removably coupled with pressurized gas source 14 (not shown in FIG. 3). In some embodiments, inlet cap 52 includes one or more retractable and/or otherwise deflectable latches 53 configured to removably couple inlet cap 52 with pressurized gas source 14. In some embodiments, as shown in FIG. 3, inlet cap 52 includes two retractable and/or deflectable latches 53 positioned on opposite sides of inlet cap 52. In some embodiments, one or more retractable and/or deflectable latches 53 are positioned at an end 55 of valve 50 and extend along axis 54 toward an opposite end 57 of valve 50. In some embodiments, retractable and/or deflectable latches 53 are configured to deflect toward an interior of inlet cap 52 to engage corresponding components of an outlet of pressurized gas source 14. In some embodiments, inlet cap 52 may include one or more engagement surfaces 59 configured to engage corresponding surfaces of pressurized gas source 14 to determine a position of valve 50 relative to pressurized gas source 14. This description of retractable and/or deflectable latches 53 and engagement surfaces 59 is not intended to be limiting. Inlet cap 52 may be coupled to pressurized gas source 14 by any method that allows valve 50 to function as described herein.

Inlet cap 52 comprises an electrical connector 56, a flow path 58, and/or other components. Electrical connector 56 and flow path 58 are both configured to removably couple with corresponding components of pressurized gas source 14. Flow path 58 is configured to receive a pressurized flow of breathable gas from pressurized gas source 14. In some embodiments, as shown in FIG. 3, flow path 58 has a cylindrical shape that extends from at or near end 55 toward opposite end 57 along axis 54. In some embodiments, flow path 58 has a cross-sectional diameter that corresponds to a diameter of an outlet of pressurized gas source 14. In some embodiments, flow path 58 has a cross-sectional diameter that is larger than a cross-sectional diameter of corresponding components of the outlet of pressurized gas source 14. In some embodiments, the cross-sectional diameter of flow path 58 is configured to allow flow path 58 to slip onto or over the corresponding components of the outlet of pressurized gas source 14 and may have any shape and/or size that allows valve 50 to function as described herein.

Electrical connector 56 is configured to receive electrical power from the pressurized gas source. In some embodiments, electrical connector 56 may be removably coupled to inlet cap 52. Electrical connector 56 is positioned on an exterior surface of inlet cap 52, not in contact with (or in minimal contact with) flow path 58. Electrical connector 56 may include one or more components and/or features configured to engage receiving features 61 on inlet cap 52. For example, electrical connector 56 may be configured be snapped and/or otherwise coupled to inlet cap 52 via receiving features 61. In some embodiments, electrical connector 56 is an off the shelf electrical component and receiving features 61 are configured to accommodate electrical connector 56 and/or other similar electrical connectors. In some embodiments, electrical connector 56 includes Molex connectors, wires, and/or other components that correspond to electrical components of heated tube 17 (FIG. 1).

In some embodiments, valve 50 includes a radial seal 81 fixed to inlet cap 52 (described below).

In some embodiments, inlet cap 52 includes one or more alignment features 63 configured to engage corresponding alignment features 65 on body 60 and/or alignment features 67 on outlet cap 68. For example, as shown in FIG. 3, inlet cap 52 includes alignment grooves 63 that are configured to engage alignment rib 65 on body 60. Alignment rib 65 is also configured to engage one of alignment grooves 67 in outlet cap 68. These alignment features are arranged on one side of one of these individual components along axis 54 and facilitate oriented coupling of inlet cap 52 to body 60, and body 60 to outlet cap 68. In some embodiments, these alignment features align electrical connector 56 of inlet cap 52 to corresponding electrical components of outlet cap 68 (described below). Alignments features 63, 65, and 67 are illustrated in FIG. 3 as grooves and a rib, but this is not intended to be limiting. Alignment features 63, 65, and 67 may have any form factor and be located in any location that allows valve 50 to function as described herein.

Body 60 is coupled to inlet cap 52. Body 60 is coupled to a side of inlet cap 52 opposite end 55. Body 60 comprises a channel 64, a plunger 66, and/or other components. Channel 64 is configured to receive the pressurized flow of breathable gas from flow path 58. Plunger 66 is biased to close flow path 58 in inlet cap 52 when the pressurized flow of breathable gas is not provided by pressurized gas source 14, or when the gas provided by pressurized gas source 14 is below a predetermined threshold level. Closing flow path 58 stops the supplemental therapy gas from flowing through inlet cap 52 toward pressurized gas source 14 when inlet cap 52 is coupled to pressurized gas source 14.

In some embodiments, body 60 comprises a spring 86 coupled to plunger 66. Spring 86 is configured to bias plunger 66 to close flow path 58 in inlet cap 52. In some embodiments, a spring force of spring 86 is configured such that plunger 66 closes flow path 58 in inlet cap 52 when a pressure of the pressurized flow of breathable provided by pressurized gas source 14 is less than the predetermined pressure threshold. Spring 86 and plunger 66 function as a one-way check valve. It should be noted that other types of one-way check valves are feasible for use with the present system. For example, other types of one-way check valves may include elastomeric flapper valves, duckbill valves, ball valves, other spring valves, and/or any other one-way check valves that allow the present system to function as described herein.

FIGS. 4A and 4B illustrate open and closed configurations of valve 50. FIG. 4A illustrates an open configuration of valve 50. FIG. 4B illustrates a closed configuration of valve 50. FIGS. 4A and 4B illustrate valve 50 coupled to pressurized gas source 14 and heated tube 17. As shown in FIG. 4A, when a therapy pressure of gas provided by pressurized gas source 14 is greater than or equal to a predetermined pressure threshold of $4 cmH_2O$ (for example), the pressure of the pressurized flow of breathable gas overcomes the spring force of spring 86 to cause plunger 66 to move away from the outlet 87 of pressurized gas source 14 to open flow path 58 and allow valve 50 to conduct the pressurized flow of breathable gas 89 to heated tube 17. This allows the pressurized flow of breathable gas 89 and oxygen (e.g., a flow of up to 15 LPM, illustrated by the dashed line in FIG. 4A) from source 15 (FIG. 1) to mix and flow to heated tube 17 and on to subject 12 (FIG. 1).

As shown in FIG. 4B, when a therapy pressure of gas provided by pressurized gas source 14 is less than 4cmH$_2$O (for example), the pressure of the pressurized flow of breathable gas does not overcome the spring force of spring 86 and plunger 66 does not move away from outlet 87 (or moves back toward outlet 87) of pressurized gas source 14 to close flow path 58. Closing flow path 58 stops the supplemental therapy gas from flowing through valve 50 toward pressurized gas source 14 when valve 50 is coupled to pressurized gas source 14. However, supplemental (oxygen) therapy gas may still be provided to subject 12 (FIG. 1). In this example, valve 50 effectively opens (relative to flow path 58) when the pressure of the pressurized flow of breathable gas 89 is at or above the predetermined pressure threshold (e.g., 4cmH$_2$O) and closes when the pressure drops below the predetermined pressure threshold (e.g., 4cmH$_2$O).

Returning to FIG. 3, in some embodiments, body 60 comprises one or more vents 80 in body 60. Vents 80 are configured to vent channel 64 to atmosphere to facilitate dispersion of the supplemental therapy gas to atmosphere and breathing of atmospheric air by subject 12 when the pressurized flow of breathable gas is not provided by pressurized gas source 14 and plunger 66 has closed flow path 58 in inlet cap 52.

As shown in FIG. 3, in some embodiments, body 60 has a generally cylindrical shape. In some embodiments, body 60 comprises an outer cylinder 83 and an inner cylinder 85, and/or other components. Outer cylinder 83 forms channel 64. Inner cylinder 85 is coupled to plunger 66 and one or more vents 80, and is in communication with channel 64, such that channel 64 is vented to atmosphere when plunger 66 closes flow path 58 in inlet cap 52, and substantially sealed from atmosphere when the pressurized flow of breathable gas is provided by pressurized gas source 14. In some embodiments, body 60 may include one or more manufacturing features 71 designed into body 60 to facilitate molding and/or other production of body 60, one more alignment and/or spacing features configured to facilitate coupling body 60 with inlet cap 52 and/or outlet cap 68, and/or other features.

In some embodiments, valve 50 includes a radial seal 81 fixed to inlet cap 52. In some embodiments, radial seal 81 may be formed from silicone and/or other elastomeric materials. In some embodiments, radial seal 81 is formed from biocompatible materials because the pressurized flow of breathable gas flowing through valve 50 may contact radial seal 81. In some embodiments, a silicone (for example) radial seal 81 is configured to substantially seal a connection between inlet cap 52 and outlet 87 from pressurized gas source 14 (shown in FIGS. 4A and 4B) such that the pressurized flow of breathable gas and/or the supplemental therapy gas do not unintentionally leak out of valve 50. In some embodiments, seal 81 may interface with plunger 66 if valve 50 is not connected to pressure source 14/outlet 87. Otherwise, plunger 66 may interface with and generally seal (e.g., a face seal) to outlet 87 and prevent flow back into pressure source 14.

In some embodiments, vents 80 may be angled to bias the vented gases to be directed away from the pressurized gas source 14, though it may also be directed parallel to the gas from pressurized gas source 14. Outlet cap 68 can have any orientation to the body though it is currently fixed to decrease the length of the connection between 56 and 70.

Outlet cap 68 is coupled to body 60. Outlet cap 68 comprises side orifice 62 (FIGS. 2A and 2B). Side orifice 62 is configured to receive supplemental therapy gas from the supplemental gas source (e.g., supplemental gas source 15 shown in FIG. 1). Outlet cap 68 includes an electrical connector 70 electrically coupled with (or configured to couple with) electrical connector 56, and a flow path 72 coupled with channel 64. In some embodiments, electrical connectors 56 and 70 are configured to be directly coupled to each other, and/or electrically coupled via wire. Outlet cap 68 is configured to removably couple with heated tube 17 such that flow path 72 conducts the pressurized flow of breathable gas and the supplemental therapy gas from channel 64 to heated tube 17, and electrical connector 70 conducts the electrical power from pressurized gas source 14 to heated tube 17 when outlet cap 68 is coupled to heated tube 17.

In some embodiments, outlet cap 68 may include one or more engagement surfaces 79 configured to engage corresponding surfaces of heated tube 17 (FIG. 1) to determine a position of valve 50 relative to heated tube 17. Electrical connector 70 and flow path 72 are both configured to removably couple with corresponding components of heated tube 17. Flow path 72 is configured to receive the pressurized flow of breathable gas and the supplemental therapy gas through body 60. In some embodiments, as shown in FIG. 3, flow path 72 has a cylindrical shape that extends from body 60 toward end 57 along axis 54. In some embodiments, flow path 72 has a cross-sectional diameter that corresponds to a diameter of an inlet of heated tube 17. In some embodiments, flow path 72 has a cross-sectional diameter that is smaller than a cross-sectional diameter of corresponding components of heated tube 17. In some embodiments, flow path 72 has a cross-sectional diameter that is larger than a cross-sectional diameter of corresponding components of heated tube 17. In some embodiments, the cross-sectional diameter of flow path 72 is configured to allow flow path 72 to slip into the corresponding components of the outlet of heated tube 17 and may have any shape and/or size that allows valve 50 to function as described herein.

Electrical connector 70 is configured to receive electrical power from electrical connector 56. In some embodiments, electrical connector 70 may be removably coupled to outlet cap 68. Electrical connector 70 is positioned on an exterior surface of outlet cap 68, not in contact with (or in minimal contact with) flow path 72. Electrical connector 70 may include one or more components and/or features configured to engage receiving features 91 on outlet cap 68. For example, electrical connector 70 may be configured be snapped and/or otherwise coupled to outlet cap 68 via receiving features 91. In some embodiments, electrical connector 70 is an off the shelf electrical component (e.g., part of and/or configured to couple with electrical connector 56), and receiving features 91 are configured to accommodate electrical connector 70 and/or other similar electrical connectors. In some embodiments, electrical connector 70 includes Molex connectors, wires, and/or other components that correspond to electrical components of heated tube 17 (FIG. 1).

It should be noted that, in some embodiments, a back side of engaging surface 79 (e.g., opposite end 57) may comprise features similar to latch 53 on inlet cap 52 configured to removably couple a heated or non-heated tube 17 with valve 50. In some embodiments, the orientation of outlet cap 68 can be any angle around axis 54, and function as described herein, even though outlet cap 68 is illustrated in FIG. 3 with electrical connectors 56 and 70 aligned. Orifice 62 is visible on the inside of outlet cap 68 in FIG. 3. In some embodiments, the tube extending out of outlet cap 68 to end 57 that forms flow path 72 may be a 22 mm ISO port similar to what is used on in pressurized gas source 14, for example.

In some embodiments, valve 50 comprises a cover 74 configured to cover body 60, at least a portion of inlet cap 52, and at least a portion of outlet cap 68. In some embodiments, the cover comprises two pieces 76, 78. Pieces 76 and 78 form opposite sides of valve 50. In some embodiments, cover 74 has a generally cylindrical shape with a cross-sectional diameter that changes along axis 74 to correspond to diameters of body 60, inlet cap 52, outlet cap 68 and/or other components of valve 50. Cover 74 includes one or more vent orifices 95 configured to align with one or more vents 80 in body 60 to facilitate gas flow into and/or out of one or more vents 80. In some embodiments, a shape of one or more vent orifices 95 corresponds to a shape of one or more vents 80 as shown in FIG. 3, for example. In some embodiments, one or both pieces 76, 78 of cover 74 include coupling components and/or features 93 configured to facilitate coupling of pieces 76 and 78 with each other, with body 60, with inlet cap 52, with outlet cap 68, and/or with other components of valve 50. In FIG. 3, these coupling components and/or features 93 are illustrated as a tab protruding from piece 78 toward end 55, various diameter variations in pieces 76 and 78, and coupling surfaces on pieces 76 and 78, but this is not intended to be limiting. Cover 74 may be coupled to other components of valve 50 in any manner that allows valve 50 to function as described herein. In some embodiments, cover 74 has a diameter 97 of about 46 mm (or about 47.5 mm if measured from axis 54—e.g., the shape is somewhat egg shaped on each end and almost circular in the middle) when it covers the components of valve 50. In some embodiments, valve 50 has an overall length 99 of about 101 mm to electrical connector 56, and about 99 mm to an end of latch 53. It should be noted that the shapes and dimensions described herein are not intended to be limiting. They are provided as examples only. The components of valve 50 described herein may have any shape or size that allows them to function as described herein.

Returning to FIG. 1, controller 20 is configured to provide information processing capabilities in system 10. As such, controller 20 may comprise one or more of a digital processor, an analog processor, or a digital circuit designed to process information, an analog circuit designed to process information, a state machine, and/or other mechanisms for electronically processing information. Although controller 20 is shown in FIG. 1 as a single entity, this is for illustrative purposes only. In some embodiments, controller 20 may comprise a plurality of processing and/or other control units. These processing and/or other control units may be physically located within the same device (e.g., pressurized gas source 14, user interface 22), or controller 20 may represent processing functionality of a plurality of devices operating in coordination.

In some embodiments, controller 20 may be configured to execute one or more computer program components. Controller 20 may be configured to execute these components by software; hardware; firmware; some combination of software, hardware, and/or firmware; and/or other mechanisms for configuring processing capabilities on controller 20.

In some embodiments, controller 20 is configured to determine one or more parameters within system 10. The one or more parameters within system 10 may comprise gas parameters related to the pressurized flow of breathable gas, breathing parameters related to the respiration of subject 12, and/or other parameters. Controller 20 is configured to determine the one or more parameters based on the output signals of sensors 18, and/or other information. The one or more gas parameters of the pressurized flow of breathable gas may comprise, for example, one or more of a flow rate, a volume (e.g., a tidal volume, a minute volume, etc.), a pressure, humidity, temperature, acceleration, velocity, and/or other gas parameters. The one or more breathing parameters may include, for example, a tidal volume, a composition, a timing (e.g., beginning and/or end of inhalation, beginning and/or end of exhalation, etc.), a duration (e.g., of inhalation, of exhalation, of a single breathing cycle, an inspiratory time, an expiratory time, a full breath time, etc.), a breath rate, a respiration frequency (e.g., a respiratory rate), a parameter indicative of respiratory effort, and/or other parameters. The information determined by controller 20 may be used for controlling pressurized gas source 14, stored in electronic storage 24, and/or used for other uses.

In some embodiments, controller 20 is configured to control pressurized gas source 14 to generate the flow of gas in accordance with a positive pressure support therapy regime. In positive airway pressure support therapy the pressurized flow of gas generated by the pressurized gas source is controlled to replace and/or compliment a patient's regular breathing. Positive airway pressure support therapy may be used to maintain an open airway in a patient so that oxygen and carbon dioxide may be exchanged more easily, requiring little and/or no effort from the patient. By way of non-limiting example, controller 20 may control pressurized gas source 14 such that the pressure support provided to subject 12 via the flow of gas comprises continuous positive airway pressure support (CPAP), bi-level positive airway pressure support (BPAP), proportional positive airway pressure support (PPAP), ventilation therapy, and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) to promote or assist tidal ventilation. In some therapy modes (e.g., PPAP), controller 20 may control pressurized gas source 14 to apply variable pressure support in which the amount of pressure delivered to the patient during inhalation and/or during exhalation is determined and delivered on a breath by breath basis. In some embodiments, controller 20 may be configured to control pressurized gas source 14 to temporarily drop the supplied pressure during exhalation (C-Flex, Airway Pressure Release Ventilation (APRV)) to reduce exhalation effort required by subject 12.

In some embodiments, controller 20 is configured to control pressurized gas source 14 to deliver staged pressure support therapy. In staged pressure support therapy, the pressure delivered by pressurized gas source 14 gradually increases over time. In some embodiments, controller 20 may control pressurized gas source 14 to switch therapy modes based on information related to the respiration of subject 12 and/or other information. For example, controller 20 may control pressurized gas source 14 to change from BPAP to CPAP after a certain number of breaths by subject 12 and/or by some external monitor, caregiver and/or alert, such as in rescue and/or apnea ventilation.

Controller 20 is configured to control pressurized gas source 14 based on information related to the output signals from sensors 18, information determined by controller 20, information entered by a user to user interface 22, and/or other information.

User interface 22 is configured to provide an interface between system 10 and subject 12 and/or other users through which subject 12 and/or other users may provide information to and receive information from system 10. Other users may comprise a caregiver, a doctor, a decision maker, and/or other users. This enables data, cues, results, and/or instructions and any other communicable items, collectively referred to as "information," to be communicated between a user (e.g., subject 12) and one or more of pressurized gas source 14, controller 20, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressurized gas source 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

Electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.), a drive (e.g., a disk drive, etc.), or a network (e.g., cloud storage). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), cloud based storage, and/or other electronic storage media. Electronic storage 24 may store software algorithms, information determined by controller 20, information received via user interface 22, and/or other information that enables system 10 to function properly. Electronic storage 24 may be (in whole or in part) a separate component within system 10 (e.g., physical and/or as part of a cloud storage system), or electronic storage 24 may be provided (in whole or in part) integrally with one or more other components of system 10 (e.g., user interface 22, controller 20, pressurized gas source 14, etc.). The information stored by electronic storage 24 may be viewed via user interface 22, via a separate computer wirelessly (and/or with wires) coupled with system 10, and/or other via other methods. The information stored by electronic storage 24 may be used, for example, to adjust settings, used by a doctor to make medical decisions, and/or for other uses.

Figure 5:
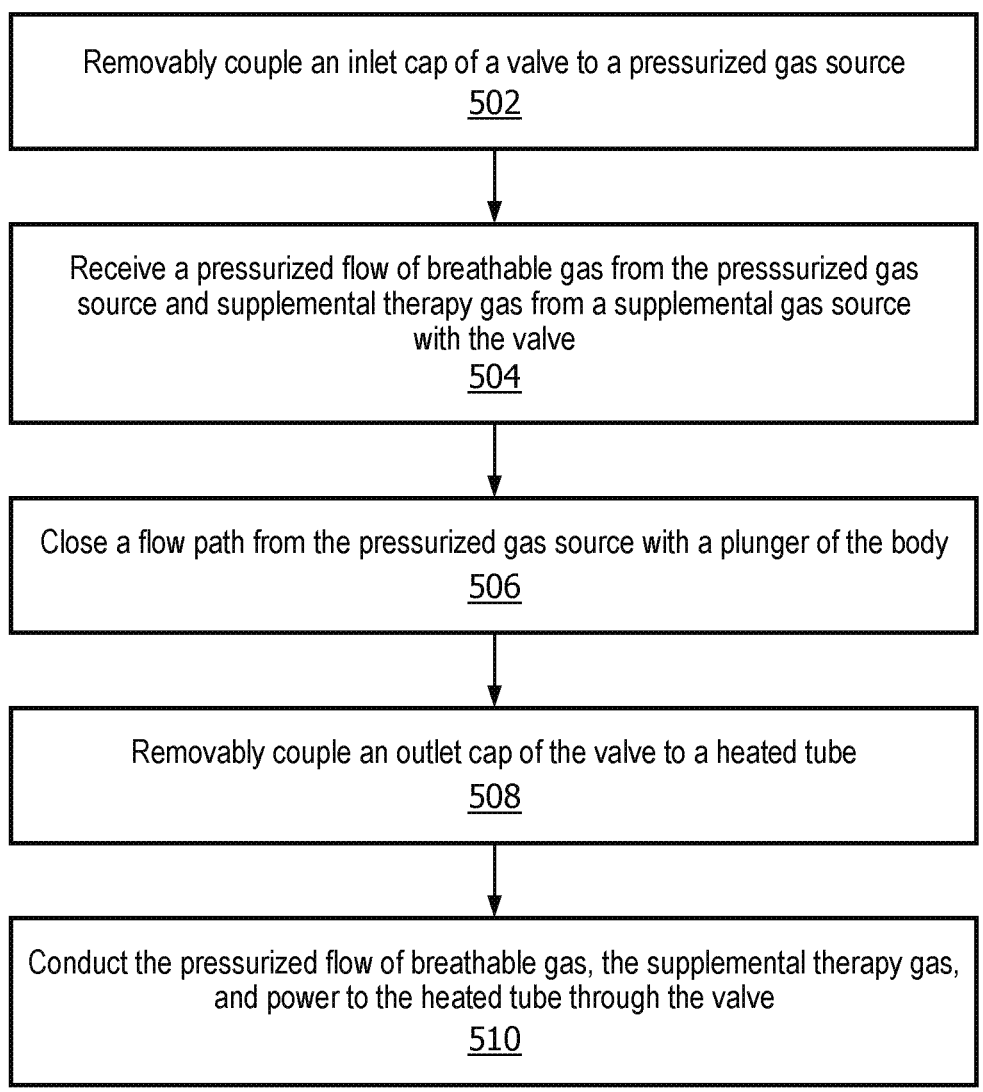
FIG. 5 illustrates a method for controlling flow in a pressure support therapy system with the valve, in accordance with one or more embodiments.

FIG. 5 illustrates a method for controlling flow in a pressure support therapy system with a valve. The pressure support therapy system comprises a pressurized gas source, a supplemental gas source, a subject interface with a heated tube and/or other components. The valve comprises an inlet cap, a body, an outlet cap and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

At an operation 502, the inlet cap is removably coupled to the pressurized gas source. In some embodiments, operation 502 includes removably coupling a first electrical connector and a first flow path of the inlet cap with the pressurized gas source. The first flow path is configured to receive a pressurized flow of breathable gas from the pressurized gas source. The first electrical connector is configured to receive electrical power from the pressurized gas source. In some embodiments, operation 502 is performed by an inlet cap the same as or similar to inlet cap 52 (shown in FIG. 3 and described herein).

At an operation 504, a pressurized flow of breathable gas from the pressurized gas source and supplemental therapy gas from a supplemental gas source is received with a channel of the outlet cap of the valve. In some embodiments, operation 504 includes receiving the supplemental therapy gas from the supplemental gas source with a side orifice of the outlet cap. In some embodiments, operation 504 is performed by an outlet cap the same as or similar to outlet cap 68 (shown in FIG. 3 and described herein).

At an operation 506, a flow path from the pressurized gas source is closed with a plunger of the body. In some embodiments, the plunger is configured to close the first flow path in the inlet cap when the pressurized flow of breathable gas is not provided by the pressurized gas source and/or the pressure provided by the pressurized gas source is below a predetermined threshold pressure. Closing the first flow path stops the supplemental therapy gas from flowing through the inlet cap toward the pressurized gas source when the inlet cap is coupled to the pressurized gas source. In some embodiments, operation 506 is performed by a plunger the same as or similar to plunger 66 (shown in FIG. 3 and described herein).

At an operation 508, the outlet cap is removably coupled to the heated tube. In some embodiments, operation 508 is performed by an outlet cap the same as or similar to outlet cap 68 (shown in FIG. 3 and described herein).

At an operation 510, the pressurized flow of breathable gas, the supplemental therapy gas, and power are conducted to the heated tube through the valve. In some embodiments, operation 510 includes coupling a second electrical connector with the first electrical connector and a second flow path with the channel. The second electrical connector and the second flow path are included in the outlet cap. The outlet cap is configured to removably couple with the heated tube such that the second flow path conducts the pressurized flow of breathable gas and the supplemental therapy gas from the channel to the heated tube and the second electrical connector conducts the electrical power from the gas source to the heated tube when the outlet cap is coupled to the heated tube. In some embodiments, operation 510 is performed by an inlet cap, a body, and an outlet cap the same as or similar to inlet cap 52, body 60, and outlet cap 68 (shown in FIG. 3 and described herein).

In some embodiments, one or more of the operations described above further comprise venting, with one or more vents of the body, the channel to atmosphere to facilitate dispersion of the supplemental therapy gas to atmosphere and breathing of atmospheric air by a subject when the pressurized flow of breathable gas is not provided by the pressurized gas source and the plunger has closed the first flow path in the inlet cap. In these embodiments, the body comprises an outer cylinder and an inner cylinder. The outer cylinder forms the channel. The inner cylinder is coupled to the plunger and the one or more vents, and in communication with the channel, such that the channel is vented to atmosphere when the plunger closes the first flow path in the inlet cap, and substantially sealed from atmosphere when the pressurized flow of breathable gas is provided by the pressurized gas source.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A valve configured for use in a pressure support therapy system, the pressure support therapy system comprising a pressurized gas source, a supplemental gas source, and a subject interface with a heated tube, the valve comprising:
   (a) an inlet cap, the inlet cap comprising a first electrical connector and a first flow path both configured to removably couple with the pressurized gas source, the first flow path configured to receive a pressurized flow of breathable gas from the pressurized gas source, the first electrical connector configured to receive electrical power from the pressurized gas source;
   (b) a body coupled to the inlet cap, the body comprising:
      (1) a channel configured to receive the pressurized flow of breathable gas from the first flow path; and
      (2) a plunger biased to close the first flow path in the inlet cap when the pressurized flow of breathable gas is not provided by the pressurized gas source or is provided at a pressure that is below a predetermined pressure threshold, wherein closing the first flow path stops supplemental therapy gas from flowing through the inlet cap toward the pressurized gas source when the inlet cap is coupled to the pressurized gas source;
   (c) outlet cap coupled to the body, the outlet cap including:
      (1) a side orifice configured to receive the supplemental therapy gas from the supplemental gas source, and
      (2) a second electrical connector electrically coupled with the first electrical connector and a second flow path coupled with the channel, the outlet cap configured to removably couple with the heated tube such that the second flow path conducts the pressurized flow of breathable gas and the supplemental therapy gas from the channel to the heated tube and the second electrical connector conducts the electrical power from the pressurized gas source to the heated tube when the outlet cap is coupled to the heated tube; and
   (d) a radial seal positioned in the inlet cap before the body, the radial seal configured to substantially seal a connection between the inlet cap and the pressurized gas source such that the pressurized flow of breathable gas and the supplemental therapy gas do not unintentionally leak out of the valve.

2. The valve of claim 1, further comprising a cover configured to cover the body, at least a portion of the inlet cap, and at least a portion of the outlet cap.

3. The valve of claim 2, wherein the cover comprises two pieces, the two pieces forming opposite sides of the valve.

4. The valve of claim 1, further comprising one or more vents in the body, the vents configured to vent the channel to atmosphere to facilitate dispersion of the supplemental therapy gas to atmosphere and breathing of atmospheric air by a subject when the plunger has closed the first flow path in the inlet cap.

5. The valve of claim 4, wherein the body comprises an outer cylinder and an inner cylinder, the outer cylinder forming the channel, the inner cylinder coupled to the plunger and the one or more vents, and in communication with the channel, such that the channel is vented to atmosphere when the plunger closes the first flow path in the inlet cap, and substantially sealed from atmosphere when the pressurized flow of breathable gas is provided by the pressurized gas source.

6. The valve of claim 1, wherein the supplemental therapy gas is oxygen.

7. The valve of claim 1, wherein the inlet cap, the body, and the outlet cap each have a generally cylindrical cross-sectional shape.

8. The valve of claim 1, wherein the first and second electrical connectors are electrically coupled via a wire.

9. The valve of claim 1, wherein the pressurized gas source comprises a pressure generator, a humidifier, or both.

10. The valve of claim 1, wherein the body further comprises a spring coupled to the plunger, the spring configured to bias the plunger to close the first flow path in the inlet cap.

11. The valve of claim 10, wherein a spring force of the spring is configured such that the plunger closes the first flow path in the inlet cap when a pressure of the pressurized flow of breathable provided by the pressurized gas source is less than the predetermined pressure threshold.

12. The valve of claim 1, wherein the inlet cap is formed along an axis of the valve, the body is coupled to the inlet cap positioned along the axis of the valve, and the outlet cap is coupled to the body opposite the inlet cap along the axis of the valve.

13. The valve of claim 1, wherein the radial seal is formed from silicone.

14. A method for controlling flow in a pressure support therapy system with a valve, the pressure support therapy system comprising a pressurized gas source, a supplemental gas source, and a subject interface with a heated tube, the valve comprising: an inlet cap, the inlet cap comprising a first electrical connector and a first flow path both configured to removably couple with a pressurized gas source, the first flow path configured to receive a pressurized flow of breathable gas from the pressurized gas source, the first electrical connector configured to receive electrical power from the pressurized gas source; a body coupled to the inlet cap, the body comprising: a channel configured to receive the pressurized flow of breathable gas from the first flow path; and a plunger biased to close the first flow path in the inlet cap when the pressurized flow of breathable gas is not provided by the pressurized gas source or is provided at a pressure that is below a predetermined pressure threshold, wherein closing the first flow path stops a supplemental therapy gas from the supplemental gas source from flowing through the inlet cap toward the pressurized gas source when the inlet cap is coupled to the pressurized gas source; an outlet cap coupled to the body, the outlet cap including: a side orifice configured to receive the supplemental therapy gas from the supplemental gas source; and a radial seal positioned in the inlet cap before the body, the radial seal configured to substantially seal a connection between the inlet cap and the pressurized gas source such that the pressurized flow of breathable gas and the supplemental therapy gas do not unintentionally leak out of the valve, the method comprising:

- removably coupling the first electrical connector and the first flow path of the inlet cap with the pressurized gas source;
- receiving the pressurized flow of breathable gas from the first flow path with the channel of the body;
- receiving the supplemental therapy gas with the side orifice of the outlet cap;
- closing, with the plunger of the body, the first flow path in the inlet cap when the pressurized flow of breathable gas is not provided by the pressurized gas source or is provided at a pressure that is below the predetermined pressure threshold, wherein closing the first flow path stops the supplemental therapy gas from flowing through the inlet cap toward the pressurized gas source when the inlet cap is coupled to the pressurized gas source; and
- coupling a second electrical connector included in the outlet cap with the first electrical connector and a second flow path included in the outlet cap with the channel, wherein the outlet cap is configured to removably couple with the heated tube such that the second flow path conducts the pressurized flow of breathable gas and the supplemental therapy gas from the channel to the heated tube and the second electrical connector conducts the electrical power from the pressurized gas source to the heated tube when the outlet cap is coupled to the heated tube.

15. The method of claim 14, further comprising venting with one or more vents of the body, the channel to atmosphere to facilitate dispersion of the supplemental therapy gas to atmosphere and breathing of atmospheric air by a subject when the plunger has closed the first flow path in the inlet cap, wherein the body comprises an outer cylinder and an inner cylinder, the outer cylinder forming the channel, the inner cylinder coupled to the plunger and the one or more vents, and in communication with the channel, such that the channel is vented to atmosphere when the plunger closes the first flow path in the inlet cap, and substantially sealed from atmosphere when the pressurized flow of breathable gas is provided by the pressurized gas source.

\* \* \* \* \*